(12) United States Patent
Hornung et al.

(10) Patent No.: US 8,303,562 B2
(45) Date of Patent: Nov. 6, 2012

(54) PANTS-TYPE DISPOSABLE SANITARY ARTICLE WITH IMPROVED FIT

(75) Inventors: Fridmann Hornung, Santiago (CL); Wolfgang Ostertag, Gerstetten (DE); Florian Kautzsch, North Caldwell, NJ (US); Benjamin Wenzel, Heidenheim (DE)

(73) Assignee: Paul Hartmann Aktiengesellschaft, Heidenheim (DE)

( * ) Notice: Subject to any disclaimer, the term of this patent is extended or adjusted under 35 U.S.C. 154(b) by 123 days.

(21) Appl. No.: 12/502,802

(22) Filed: Jul. 14, 2009

(65) Prior Publication Data

US 2009/0275911 A1  Nov. 5, 2009

Related U.S. Application Data

(63) Continuation of application No. PCT/EP2008/000254, filed on Jan. 15, 2008.

(30) Foreign Application Priority Data

Jan. 16, 2007 (DE) .......... 10 2007 002 290

(51) Int. Cl.
*A61F 13/15* (2006.01)
(52) U.S. Cl. ......... 604/385.27; 604/385.01; 604/385.24; 604/385.25; 604/385.26
(58) Field of Classification Search .......... 604/358, 604/385.01, 385.24, 385.25, 385.27, 385.29, 604/396
See application file for complete search history.

(56) References Cited

U.S. PATENT DOCUMENTS

| 4,795,454 A | 1/1989 | Dragoo |
| 4,846,825 A | 7/1989 | McMorrow |
| 5,397,318 A * | 3/1995 | Dreier ............ 604/385.19 |
| 5,622,581 A | 4/1997 | Ducker |
| 5,634,917 A | 6/1997 | Fujioka |
| 5,904,675 A | 5/1999 | Johnson |
| 6,117,121 A * | 9/2000 | Faulks et al. ........ 604/385.29 |
| 6,179,820 B1 * | 1/2001 | Fernfors ............ 604/385.27 |
| 6,217,690 B1 | 4/2001 | Rajala |
| 6,409,711 B1 | 6/2002 | Jönbrink |
| 7,094,227 B2 | 8/2006 | Ishiguro |
| 2002/0045872 A1 | 4/2002 | Shimada |
| 2004/0193135 A1* | 9/2004 | Van Gompel ........ 604/391 |
| 2005/0075618 A1 | 4/2005 | Kenmochi |
| 2006/0161128 A1 | 7/2006 | Soga |

(Continued)

FOREIGN PATENT DOCUMENTS

DE 102004032377.1 6/2004

(Continued)

OTHER PUBLICATIONS

International Search Report—PCT/EP2008/00254.

(Continued)

*Primary Examiner* — Loan Thanh
*Assistant Examiner* — Peter S Vasat
(74) *Attorney, Agent, or Firm* — Brinks Hofer Gilson & Lione (57) ABSTRACT

The disclosure relates to a disposable absorbent hygiene item in the form of a pair of knickers, said item comprising a central absorption part, an outer envelope forming a base structure comprising a waist edge which is closed all the way round in the peripheral direction and forms an opening for the waist, a rear part and a front part comprising longitudinal lateral edge sections, and a connecting region arranged between the front part and the rear part and forming the leg openings.

24 Claims, 5 Drawing Sheets

U.S. PATENT DOCUMENTS

2006/0277662 A1 * 12/2006 Coccia .............................. 2/300

FOREIGN PATENT DOCUMENTS

| EP | 0437771 | 7/1991 |
|---|---|---|
| EP | 0516877 | 12/1992 |
| EP | 0692233 | 9/1998 |
| EP | 0901780 | 3/1999 |
| EP | 0969784 | 1/2000 |
| EP | 11840217 | 3/2002 |
| EP | 1199058 | 4/2002 |
| EP | 1308148 | 5/2003 |
| EP | 0626161 | 7/2006 |
| GB | 2159693 | 12/1985 |
| GB | 2276529 | 10/1994 |
| JP | 09024063 | 1/1997 |
| WO | 96/34588 | 11/1996 |
| WO | 02/49560 | 6/2002 |
| WO | 03/063748 | 7/2003 |

OTHER PUBLICATIONS

Search Report—DE 10 2007 002 290.7.
Search Report—EP 1308148.
Search Report—EP 1199058.
Search Report—EP 01307476.
Search Report—WO 96/34588.

* cited by examiner

PANTS-TYPE DISPOSABLE SANITARY ARTICLE WITH IMPROVED FIT

CROSS-REFERENCE TO RELATED APPLICATIONS

This application is a continuation of International Application No. PCT/EP2008/000254 filed on Jan. 15, 2008, which claims the benefit of DE 10 2007 002 290.7, filed Jan. 16, 2007. The disclosures of the above applications are incorporated herein by reference.

FIELD

The present disclosure relates to a disposable, pants-type, absorbent sanitary article for adults.

BACKGROUND

The statements in this section merely provide background information related to the present disclosure and may not constitute prior art.

Sanitary pants-type articles mostly comprise multiple elasticizing means, frequently in the form of elastic strands, which are mostly connected pretensioned to basically non-elastic chassis materials in an adhesive manner. Typically, a hip edge region is preferably elasticized all around the periphery. In the known diaper pants, elasticizing means are also provided in the front region and in the rear region. Likewise, the periphery surrounding the leg openings and/or the periphery forming the leg openings are at least configured to be elastic in sections, such that a sealing fit of the sanitary article onto the user's skin surface is ensured in order to prevent lateral leaking of excretions from the body. Stand-up cuff elements which, apart from the elastic leg openings, offer further lateral leak protection have already been used in known diaper pants (for example in EP-1184017-A1, EP-1199058-A1, EP-1308148-A2).

It is further known how to provide elasticizing means essentially stretching in the transverse direction between the hip edge and the crotch region in order to improve the fit of the sanitary article in terms of a body-facing arrangement.

Nevertheless, the fit problems of disposable pants-type sanitary articles for adults have still not been adequately solved despite the use of several elastic components. Precisely in the crotch region, i.e. where the fit and reliability of fluid absorption are conflicting target parameters, the already known sanitary articles have not provided adequate solutions yet.

SUMMARY

On that basis, it is the object of the present disclosure to improve the wearing comfort of absorbent sanitary articles of the above mentioned type.

The present disclosure provides improved wearing comfort of absorbent sanitary articles with a pants-type sanitary article, wherein the front crotch region has a strand or ribbon-shaped elasticizing means which are arranged along a first section of the respective leg opening and wherein the rear crotch region has a second strand or ribbon-shaped elasticizing means which are arranged along a second section of the respective leg opening, and the rear crotch region between the respective longitudinal edge of the absorbent core and the respective leg opening has an elastic element which is arranged from a region close to the leg opening in a direction having a transverse component toward the central longitudinal axis as well as a longitudinal component toward the back piece. Thus, this elastic element runs transversely backward.

The interaction of the strand or ribbon-shaped elasticizing means elasticizing the leg opening section and the elastic element effectively prevents that there, where it strongly tends to undesirable folding, i.e. in the rear crotch region outside the absorbent core, the chassis-forming wrap in pants-type sanitary articles for adults with a very narrow absorbent core is transversely forced in the direction of the back piece. It has surprisingly been found that for the vast majority of users this clearly stands in good stead for the fit of the sanitary article.

The width of the absorbent core in particular at the height of the central transverse axis amounts to about 10 cm, furthermore in particular at least about 12 cm and especially at least about 13 cm, but at most about 18 cm, in addition in particular at most about 17 cm, furthermore in particular at most about 16 cm, still furthermore in particular about 15 cm, and also in particular at most about 14 cm; it thus has a comparatively narrow configuration.

Within the scope of the present disclosure, the absorbent core is understood to be the part of the sanitary article intended for permanent absorption and storage of the excreted body fluids. The absorbent core usually contains superabsorbent materials (SAP), in particular a fiber mixture, in particular cellulose fibers, and in particular in the form of cellulose fluff. If the sanitary article comprises a multi-part or multi-layered absorbent core, the absorbent core is considered to be the layer or the part of the absorbent core, which, according to the specifications, permanently stores most part of the secreted body fluid.

A further form of the present about provides that the rear crotch region has an inner area immediately adjacent to the central transverse axis and an outer area adjacent to the inner area which extends in the longitudinal direction to the back piece, and whereby the second strand or ribbon-shaped elasticizing means which are arranged along a second section of the respective leg opening, as well as the elastic element, are exclusively arranged in the outer area. The chassis-forming wrap usually has a larger width in the outer area of the rear crotch region than in the inner area of the crotch region. The above mentioned problem of the chassis-forming wrap folding laterally outside the absorbent core is thus especially pronounced there. In a further development of this inventive concept, the transverse distance between the edge of the absorbent core and the respective leg opening is at least about 5 cm in the outer area, in particular at least about 7 cm, and further in particular at least about 9 cm.

In another form of the present disclosure, the length of the longitudinal components of the elastic element is about 2.5 to about 21.0 m, in particular about 4.5 to about 19.0 cm, furthermore in particular about 6.5 to about 17.0 cm, and further in particular about 7.5 to about 15.0 cm. Furthermore, the length of the transverse component of the elastic element is preferably about 2.0 to about 18.0 cm, in particular about 4.0 to about 15.0 cm, further in particular about 5.0 to about 13.0, and further in particular about 6.0 to about 12.0 cm.

The interaction of the second strand or ribbon-shaped elasticizing means and the elastic element proves especially effective, if the elastic element is formed by a further extension of the second strand or ribbon-shaped elasticizing means, as they run along the second section of the respective leg opening in the direction of the central transverse axis in the first instance, and subsequently run configured in a U or V-shape from the area close to the leg opening in a direction that has a transverse component toward the central longitudinal axis, as well as a longitudinal component toward the back piece. In the state donned by the user, a pouch that is only open on one side may then form between the thighs and the U or V-shaped configuration which serves for absorbing fluid or feces leaking from the lateral edge of the absorbent core.

In a further development of the inventive concept, it is advantageous that the inner area of the rear crotch region of the respective leg opening has a third strand or ribbon-shaped elasticizing means which are arranged along a third section of the respective leg opening. These third strand or ribbon-shaped elasticizing means are exclusively arranged in the inner area of the rear crotch region.

The strand or ribbon-shaped elasticizing means elasticizing the leg opening sections may in particular be formed of a skein of about 2-7, in particular about 2-6, furthermore in particular about 2-5 and especially in particular about 2-4 of especially thin elastic strands, like Lycra® or Spandex® yarn of the strength about 300-1500 dtex, in particular about 500-900 dtex running parallel to one another at a close distance of about 1-20 mm, in particular of about 2-15 mm, furthermore in particular of about 3-10 mm and still further in particular of about 5-7 mm which are affixed to the chassis-forming wrap material pretensioned at about 1.5-4.5, in particular at about 2.0-4.0.

The extension of the first, second and third elasticized sections of the respective leg opening in the longitudinal direction of the sanitary article is selected especially such that the sum of the lengths of the first to third sections of the respective leg opening is about 20-60 cm, in particular about 25-55 cm, furthermore in particular about 27-50 cm, and also in particular about 29-48 cm.

In a further development of this inventive concept, it has further proven advantageous for the wearing comfort, if the relationship between the sum of the lengths of the first to third sections of the respective leg opening and the perimeter of the respective leg opening is at most about 0.7, in particular at most about 0.6, furthermore in particular at most about 0.55, and also in particular at most about 0.5.

In a further development of the present disclosure it is provided that the first, second and third strand or ribbon-shaped elasticizing means are separated from one another in the longitudinal direction, such that between the first and third and between the second and third strand or ribbon-shaped elasticizing means a nonelastic leg opening section is provided. Against the background that modern sanitary articles additionally have so-called "cuff elements" basically stand-up cuffs running in the longitudinal direction which form a lateral barrier against the leakage of fluids and also solid excretions from the body, it does not seem strictly necessary to continuously elasticize the leg openings all around the periphery. Since elasticizing means cause ruffling or ruching of the materials they are joined to, if they are joined to those materials in the pretensioned state, they cause an accumulation of material in the relaxed state which may, for example, be uncomfortable in the sitting position. In any case, when the user moves, ruffled or ruched areas, i.e. elasticized areas, notably rub against the user's skin and may cause skin irritations. Thus an overall better wearing comfort is accomplished by means of the nonelastic leg opening sections.

It has proven convenient and advantageous, if the first elasticizing means are at a greater distance from the third elasticizing means in the longitudinal direction than the second elasticizing means from the third elasticizing means, since the risk of undesirable material accumulation in the center of the crotch region is considered to be particularly high.

The course of the third elasticizing means advantageously is to a large extent mirror-inverted with respect to the course of the elastic element, the axis of symmetry being a central line extending transversely between the second elasticizing means and the elastic element. Surprisingly, this is especially advantageous for the fit of the sanitary article. A balance of the elastic forces is evidently accomplished in this way.

It further proves advantageous, if the chassis-forming wrap in the back piece and/or in the front piece and especially also in an area of the crotch region adjacent to the back piece and/or back piece has transverse strand or ribbon-shaped elasticizing means. The fit of the sanitary article may thus be further improved in terms of a body-facing arrangement. Such an elasticizing means may cause an intended contraction of the absorbent core in the crotch region. If no ruffling of the absorbent core is desired, insofar as the elasticizing means run underneath the absorbent core, the elasticizing effect of the elasticizing means may be removed, or, more particularly, severed. The elasticizing means will then relax and/or bounce, insofar as they are not joined to the external wrap in that section. The severing may, for example, be performed by means of a single cut. It would, however, be conceivable and advantageous that the severing of the elasticizing means is carried out by means of multiple cuts so that the elasticizing means continuously stretched beforehand are divided into multiple small sections, in particular with millimeter-scale lengths, thus losing their elasticizing effect. In such cases the elasticizing means may also be joined to the external wrap in an adhesive manner without impeding relaxation. Simple or multiple cutting of the elasticizing means may also be carried out by means of laser processing. In an alternative embodiment, the elasticizing effect of the previously stretched elasticizing means is removed by means of heat and/or pressure and/or ultrasound.

In another form of the present disclosure, it is provided that the rear crotch region has a larger longitudinal extension than the front crotch region. If a front and/or rear crotch region are mentioned previously or hereinafter in this document, the following shall be understood: As described above, the sanitary article according to the present disclosure comprises a chassis-forming external wrap with a front piece, a back piece, and a crotch region between the front piece and the back piece forming the leg openings when viewed in the longitudinal direction. Front piece and back piece are the chassis areas whose longitudinal side edge sections are joined together by the manufacturer to form the closed pants-shape. The crotch region may theoretically be divided by a central transverse axis running in the transverse direction into a front crotch region and a rear crotch region, whereby the central transverse axis runs in the transverse direction along a minimum, i.e. the smallest, width of the crotch region. In pants-type sanitary articles whose crotch area is rectangular, the central transverse axis is placed such that it divides the rectangular area in the longitudinal direction. In pants-type sanitary articles which do not allow positioning the central transverse axis either according to the first or to the second method, the position of the central transverse axis is determined according to the method described in EP0969784B1, Section [0038], with reference to FIG. 4. The crotch point is determined in this way. The central transverse axis is located at the height of this crotch point. Thus, the length of the rear crotch region is the section that extends from the central transverse axis to the beginning of the back piece when viewed in the longitudinal direction. The length of the front crotch region is analogous, the extension of the crotch region starting from the central transverse axis up to the beginning of the front piece.

In a further development of this inventive concept, it has proven advantageous with regard to the fit of the sanitary article, if the rear crotch region has a length of about 20-50 cm, in particular a length of about 22-45 cm, and furthermore in particular a length of about 26-39 cm. The inner and/or outer areas of the rear crotch region advantageously have a length of about 8-30 cm, in particular about 10-25 cm, and furthermore in particular 1 about 2-22 cm.

It is further advantageous for the fit of the sanitary article, if the relationship between the length of the inner area of the crotch region and the length of the outer area of the rear crotch region is between about 0.4 and about 0.6, in particular between about 0.45 and about 0.55, and furthermore in particular between about 0.47 and about 0.52.

In a further advantageous form of the present disclosure it is provided that the first and/or second and/or third strand or ribbon-shaped elasticizing means transverse the crotch region underneath the absorbent core starting from a first leg opening to take a mirror-inverted course with respect to the central longitudinal axis along the other second leg opening on the opposite side. In such cases, the absorbent core may be ruffled in the crotch region. On the other hand, it may likewise be advantageously provided that the elasticizing effect of the elasticizing means running underneath the absorbent core may be at least removed in sections, in particular by means of heat and/or pressure and/or laser processing and/or ultrasound and/or cutting, or that the elasticizing means underneath the absorbent core are tension-free. In such cases undesired ruffling of the absorbent core may be avoided.

Cuff elements with an elastic cuff section may be advantageously provided on both sides of the absorbent core and stretched in the longitudinal direction. Stand-up cuff elements of this type which apart from leg openings offer a further lateral leak protection have already been used in known pants-type sanitary articles and are, for example, known from EP11840217, EP1199058 or EP1308148.

In another form, the absorbent core is arranged with its garment-facing side to the body-facing layer of the chassis-forming outer wrap and preferably affixed to it at least in sections by means of adhesives, like hot melting adhesives or other joining processes, like thermal welding.

The absorbent core comprises body fluid-absorbent materials, like synthetic fibers, in particular cellulose fibers, preferably in the form of cellulose fluff. Besides, the absorbent core comprises superabsorbent materials (SAP), in particular based on tensioactive, partially neutralized polyacrylates.

The absorption core is at least covered in sections by a liquid pervious topsheet and is furthermore preferably underpinned, at least in sections, by a liquid impervious backsheet when worn. The topsheet in particular comprises non-woven material or foil materials provided with openings. The backsheet particularly comprises a foil, in particular having a thickness of at most about 15 μm. The backsheet may advantageously also contain during use, or consist of, liquid impervious but also water-vapor pervious, non-woven materials, like meltblown layers (M) and spunbond layers (S), in particular laminates made of meltblown and spunbond layers, like SM or SMS or SMMS laminates. The backsheet in particular comprises during use a liquid pervious but also breathable, i.e. water-vapor pervious, particularly microporous foil. The water-vapor permeability of the backsheet in particular is at least about 300 g/m$^2$/24 h, also in particular at least about 1000 g/m$^2$/24 h, furthermore in particular at least about 2000 g/m$^2$/24 h, in addition especially at least about 3000 g/m$^2$/24 h, also in particular at least about 4000 g/m$^2$/24 h, and furthermore in particular at least about 6000 g/m$^2$/24 h, measured according to DIN 53 122-1 (version 2001-08).

The optionally provided cuff elements extend along both sides of the absorbent core and are in particular affixed with their proximal edges to each longitudinal edge of the body-facing side of the absorbent core, in particular to the topsheet. In an alternative further development of the present disclosure, the proximal edges of the cuff elements are affixed to both sides outside the absorption core, in particular to the body-facing side of the chassis-forming outer wrap. The distal, at least sectionally stand-up edges facing the user, preferably have elasticizing means, in particular strand or ribbon-shaped elasticizing means of the type mentioned above. In an alternative embodiment, the cuff elements comprise, or consist of, massive elastic material, like an elastic foil or elastic nonwoven fabric.

The distal edge of the cuff elements is tilted inward in the direction of the longitudinal axis of the sanitary article. This is thereby provided in that, in one or both end sections the distal edge of the cuff elements is affixed inward to the body-facing side of the absorbent core, in particular to the topsheet. By affixing the end sections of the cuff elements over a sufficiently large section on the absorbent core, the elastic effect may at the same time be removed from this section in a form of the present disclosure, whereby this affixed end section forms a nonelastic cuff element.

According to a further inventive concept, in the front crotch region, at the respective leg opening, the pants-type sanitary article has a region close to the hip opening, a region close to the crotch center and a central region arranged in between, whereby the region close to the hip opening, the region close to the crotch center and the central region exhibit elasticizing means and whereby the resulting forces of elasticizing means respectively exhibit a component in the transverse direction, and whereby this component is larger in the transverse direction in the region close to the hip opening than in the central region and/or in the region close to the crotch center, and the component in the transverse direction is larger in the central region than in the region close to the crotch center. An additional region may in particular extend from the region close to the crotch center to the central transverse axis, where the leg openings have no elasticizing means at all. This particularly favors the fit of the sanitary article. In particular, the elasticizing means in the region of the leg openings close to the hip opening should exclusively be formed by strand or ribbon-shaped elasticizing means essentially arranged in the transverse direction. In a further development of this inventive concept it proves advantageous, if the elasticizing means in the central region are formed by a section of the strand or ribbon-shaped elasticizing means close to the hip opening, as well as by strand and ribbon-shaped elasticizing means essentially arranged in the transverse direction. On the other hand, the elasticizing means in the region close to the crotch center are exclusively formed in particular by a section of the first strand or ribbon-shaped elasticizing means close to the crotch center.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

FIGS. 1-5 show a pants-type sanitary article for adults overall designated by the reference numeral 2, in a flat-out, stretched state of the longitudinal edge sections 16, 18 joined together by the manufacturer. FIGS. 1-5 respectively show the same sanitary article, where each shows different details for the sake of overview. It should be noted that all preceding and hereinafter specified and claimed dimensions of the sanitary article refer to this flat-out, stretched state. FIG. 6 shows the sanitary article after joining together the longitudinal side edge sections 16, 18.

The sanitary article 2 comprises an outer chassis-forming wrap 21 with a back piece 4, a front piece 6, and an intermediate crotch region 10 delimitating the subsequent leg openings 8a, b. In the flat-out state, the back and front piece are delimited by longitudinal side edges 12. They are joined together in the region of the longitudinal side edge sections 16 and/or 18 to form the pant shape, possibly by means of heat sealing or other usual joining processes. In this way, two side seam regions 60 (FIG. 6) of the sanitary article 2 are formed that cannot be separated without being destroyed. The finished sanitary article may, however, by all means have a predetermined break line, in particular along these side seam regions, in order to open the sanitary article from the donned state. In addition any closing elements, like adhesively or mechanically adherent closure tabs, may in principle be provided to again close the sanitary article after having opened it like a diaper of the open form. From the manufacturer's perspective, the sanitary article is, however, produced as pants and therefore has a hip edge 20 formed by the front hip edge 20a and the rear hip edge 20b which is excluded all around the periphery and forms a hip opening 50 delimited on all sides.

Figure 1:
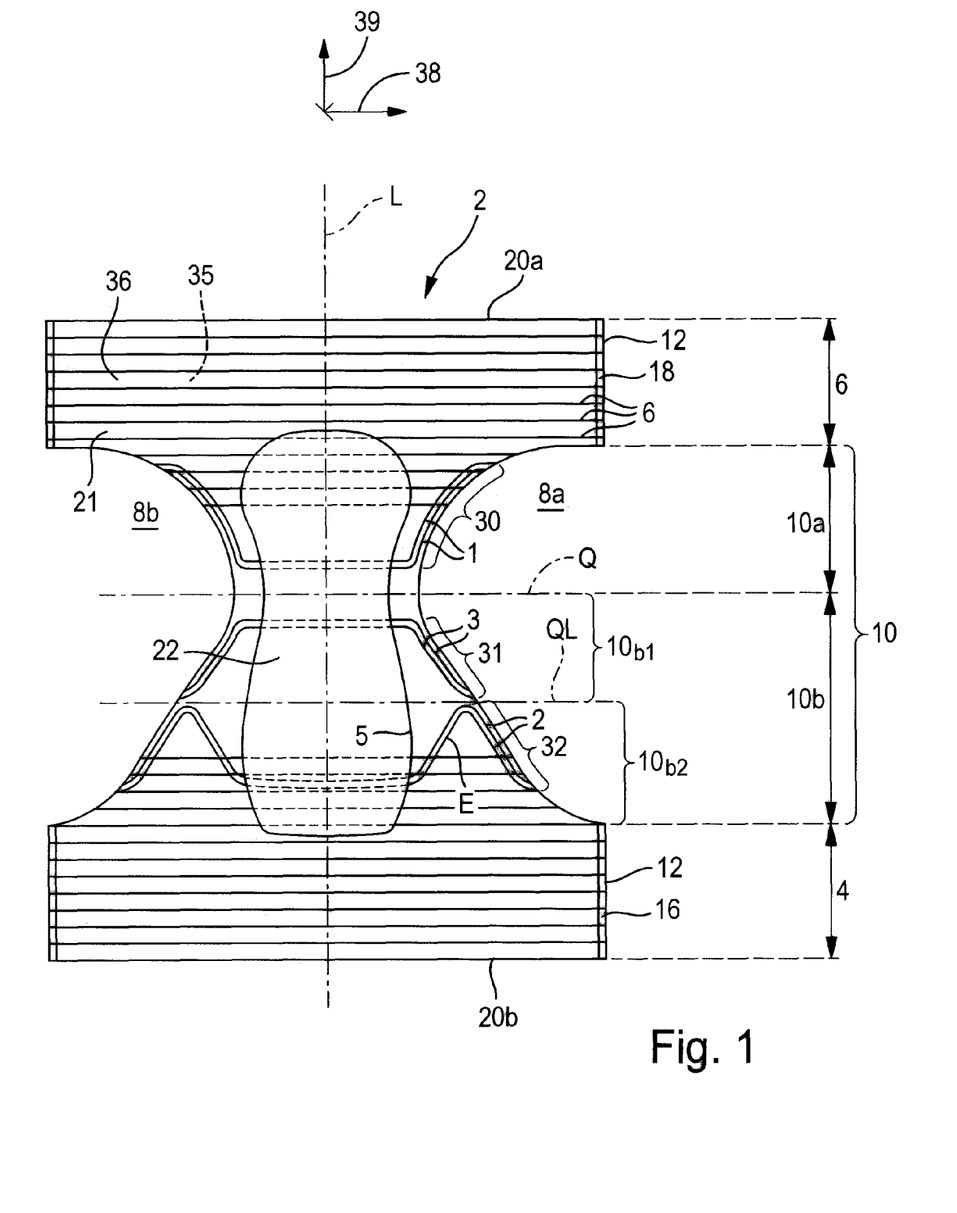
FIG. 1: A plan view of an embodiment of the sanitary article according to the present disclosure in a flat-out, extended state of the longitudinal edge regions joined together by the manufacturer.
Figure 2:
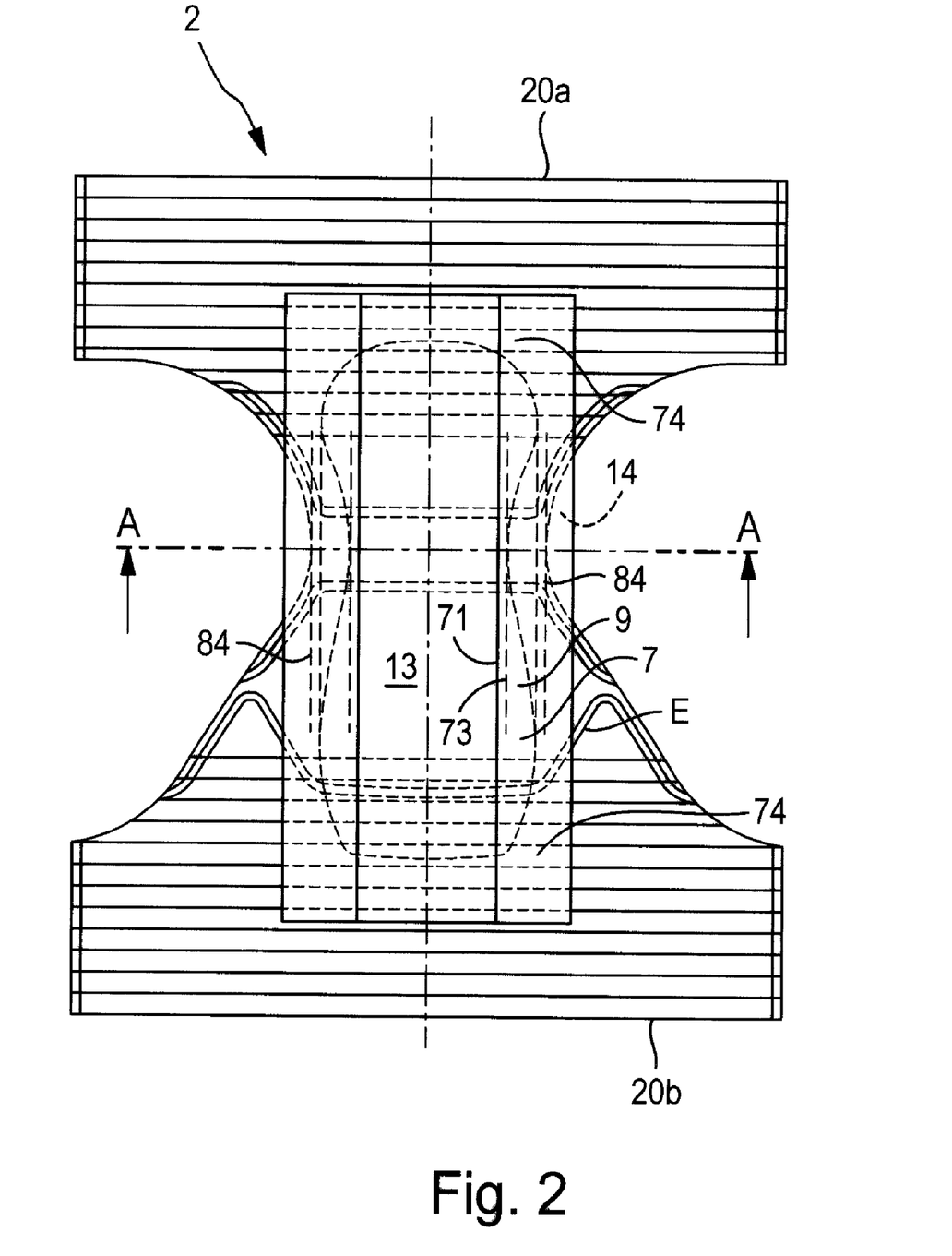
FIG. 2: A view corresponding to FIG. 1 reproducing the topsheet and backsheet wrapping the absorbent core.
Figure 3:
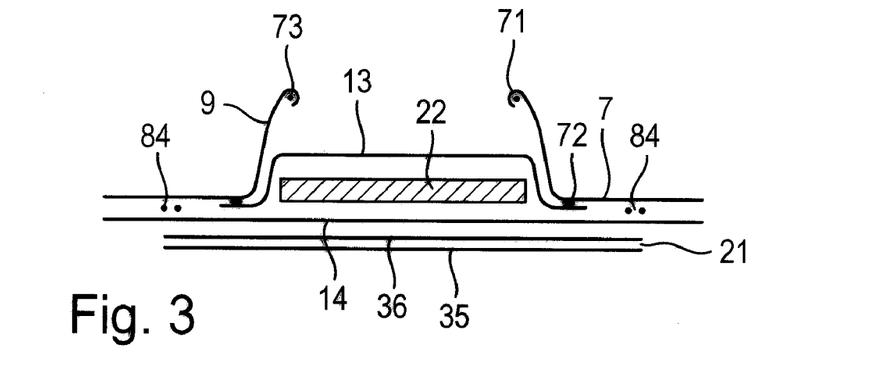
FIG. 3 A sectional view of FIG. 2 along A-A.

The sanitary article 2 further comprises an absorbent core 22 which is affixed to the body-facing side of the outer wrap 21. As shown in FIGS. 2 and 3, but not in FIGS. 1, 4 and 5, for its part, the absorbent core 22 has a liquid impervious backsheet 14 and a liquid pervious topsheet 13.

With its garment-facing side, i.e. the side of the backsheet 14 facing away from the body, the absorbent core 22 is joined as a functional and prefabricated unit to the body-facing side of the outer wrap 21.

The outer wrap 21 forming the diaper chassis continuously extends from the front hip edge 20a to the rear hip edge 20b and, in the present description, comprises a double-ply nonwoven laminate consisting of a body-facing inelastic nonwoven layer 36 and a nonelastic garment-facing nonwoven layer 35 with a grammage of 22 g/m² each which are at least joined together in sections. Within the scope of the present disclosure, a nonelastic material like nonwoven or foil is understood to be a material that after one-time stretching of a 25-mm wide material strip at a strain rate of 500 mm/min either breaks or, after subsequent immediate release, is permanently stretched by at least 7.5%. This means that, for example, a 100-mm long material strip which was stretched to a length of 130 mm is at least 107.5 cm long after release.

Elastic strands 6 which are affixed between both the nonwoven layers 35, 36 that were pretensioned by means of hot-melt contact adhesive extend in the transverse direction 38 from each hip edge 20a, 20b into the crotch region 10.

In the longitudinal direction 39, the back piece 4 of the sanitary article has an extension of 17 cm. The length of the front piece 6 likewise is 17 cm. The crotch region 10 between the front and back piece is divided by the central transverse axis Q into a rear crotch region 10b and a front crotch region 10a. The central transverse axis Q runs in the transverse direction 38 perpendicular to the central longitudinal axis L at the height of the minimum width of the crotch region 10 of the chassis-forming wrap 21. The central longitudinal axis L is an imaginary line parallel to the longitudinal direction 39 which divides the transverse extension of the chassis-forming wrap 21, i.e. its width at that point, at the height of the central transverse axis. In the longitudinal direction 39, the front crotch region 10a has an extension of 17.5 cm. In the longitudinal direction 39, the rear crotch region 10b has an extension of 29 cm.

Figure 4:
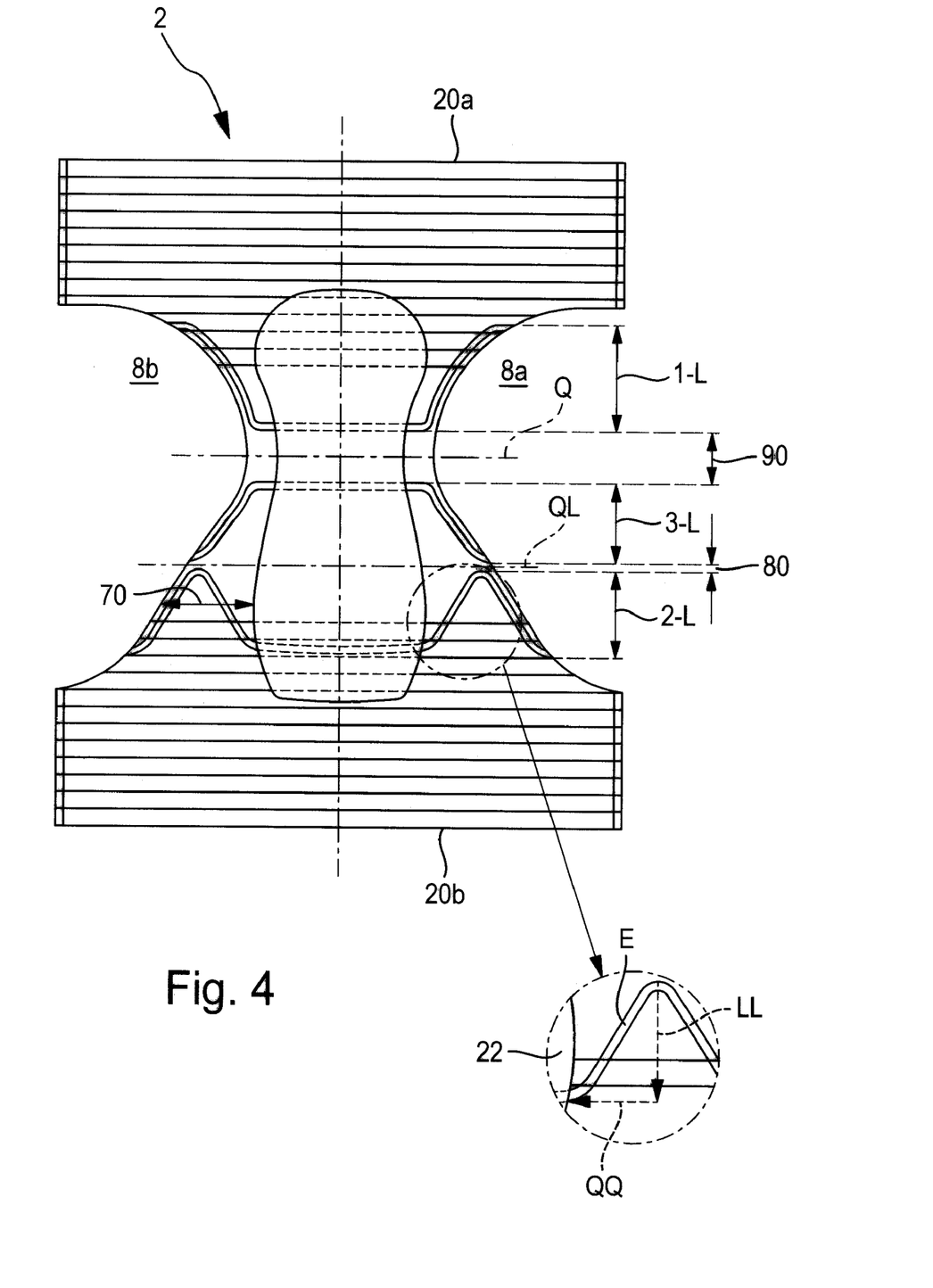
FIG. 4 A view corresponding to FIG. 1 indicating the lengths of the elasticizing means.

Each leg opening 8a, 8b has first strand-shaped elasticizing means 1 along the first section 10 which, in the pretensioned state, are affixed between the nonwoven layers 35, 36 that form the chassis-forming wrap 21. Those first elasticizing means 1 are exclusively arranged in the front crotch region 10a. In an outer area 10b2 along a second section 32, the rear crotch region 10b of the respective leg opening 8a, b, has second strand-shaped elasticizing means 2 that are different form the first means which likewise are affixed in the pretensioned state to the chassis-forming wrap 21. Those second elasticizing means 2 run transversely backward forming a v-shaped configuration from an area close to the leg opening and in the outer area 10b2 between the longitudinal edge 5 of the absorbent core and the leg opening thereby form an elastic element E whose extension from the area close to the leg opening has a transverse component QQ, i.e. a component in the transverse direction 38, in the direction of the central longitudinal axis L, as well as a longitudinal component LL, i.e. a component in the longitudinal direction 39, and in the direction of the back piece 4 (FIG. 4). The length of the transverse component QQ is 6.7 cm; the length of the longitudinal component LL is 9.0 cm. The elastic element E is thus formed by a further extension of the second elasticizing means 2. The effect of this arrangement of elastics is indicated schematically in FIG. 6 by the forces P1 and P2 which smooth out the diaper chassis in the area outside the absorbent core in the critical region that tends to folding and thus apply it tightly to the user's body. In pants-type sanitary articles, the critical region tending to fold is problematic where the distance 70 (FIG. 4) in the rear crotch region 10, in particular in the outer area 10b2 of the rear crotch region 10b between the absorbent core 22 and leg opening 8a, b, is greater than 5 cm in the transverse direction 38, in particular greater than 7 cm and further in particular greater than 9 cm and thus relatively large surface sections of the chassis-forming wrap 21 are at risk of folding.

The width of the absorbent core, i.e. its extension in the transverse direction, at the height of the central transverse axis Q, amounts only to 14 cm. The width of the chassis-forming wrap 21 is 22 cm at that point.

In the rear crotch region 10b, the sanitary article 2 has in addition a third strand-shaped elasticizing means 3 that are different from the first and second elasticizing means and which run along a third section 31 of the respective leg opening 8a, 8b. These third elasticizing means 3 are exclusively arranged in an inner area 10b1 of the rear crotch region 10b, whereas the second elasticizing means 2 are exclusively arranged in an outer area 10b2 of the rear crotch region 10b.

It may be noticed that a transverse axis QL forms the limit between the inner area 10b1 and the outer area 10b2 of the rear crotch region 10b. The transverse axis QL runs centrally between the second and third elasticizing means 2, 3 separated from one another in the longitudinal direction by the distance 80 (FIG. 4) and forms an axis of symmetry relative to the course of the third elasticizing means 3 and the elastic element E. In this case, the distance 80 is 1.5 cm.

In the longitudinal direction 39, the inner area 10b1 of the rear crotch region 10b has an extension of 14.3 cm. In the longitudinal direction 39, the outer area 10b2 of the rear crotch region 10b has an extension of 14.7 cm.

It may be noticed that the first, second and third strands or ribbon-shaped elasticizing means 1, 2, 3 traverse the crotch region 10 underneath the absorbent core 22 from the first leg opening 8a to take a mirror-inverted course relative to the central longitudinal axis L along the other second leg opening 8b on the opposite side. Underneath the absorbent core 22, the elasticizing effect of the elasticizing means 1, 2, 3 is removed at least in sections by means of heat and/or pressure and/or laser processing and/or ultrasound and/or cutting. It would also be conceivable that the elasticizing means 1, 2, 3 are tension-free at that point.

The first elasticizing means 1 are longitudinally spaced apart from the third elasticizing means 3 by a distance 90 of 6.0 cm (FIG. 4).

The maximum extension in the longitudinal direction 39 of the first, second and third elasticizing means is indicated in FIG. 4 as 1-L, 2-L and 3-L. In this case, a significant section of the leg openings 8a, 8b has no elasticizing means with a component in the longitudinal direction 39. This ensures that, with still sufficient elasticity of the leg opening, no excessive folding with consequent skin irritations results when worn. The sum of the lengths (1-L+2-L+3-L) is only 31.5 cm. The perimeter of the respective leg opening is 68.9 cm. The perimeter of the respective leg opening is thus 48.2% greater than the extension of the crotch region 10 in the longitudinal direction 39 which is only 46.5 cm. The relationship between the sum of the lengths 1-L+2-L+3-L and the length of the perimeter of the respective leg opening is thus only 0.46.

Figure 5:
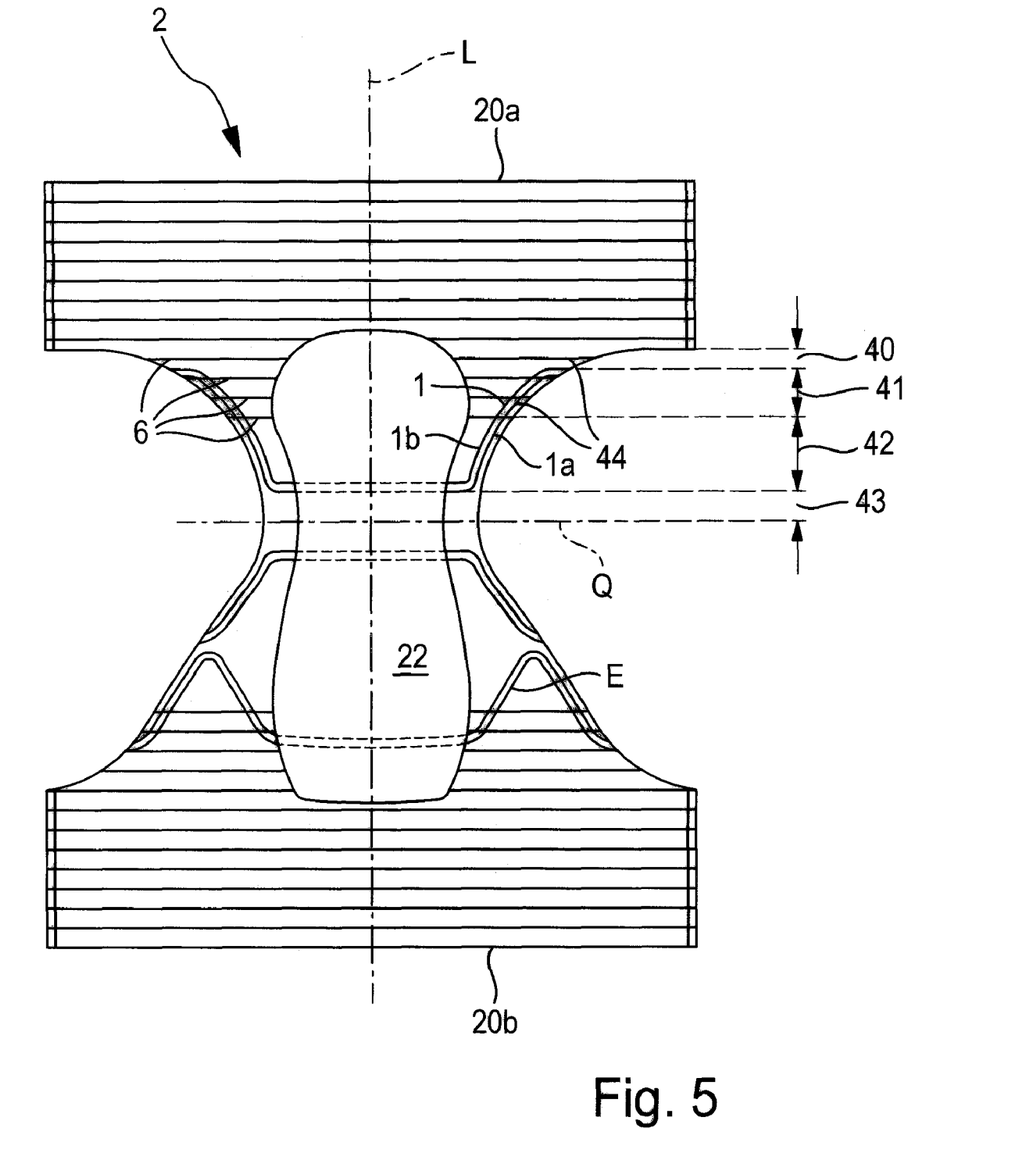
FIG. 5 A further view corresponding to FIG. 1 indicating the leg opening regions.
Figure 6:
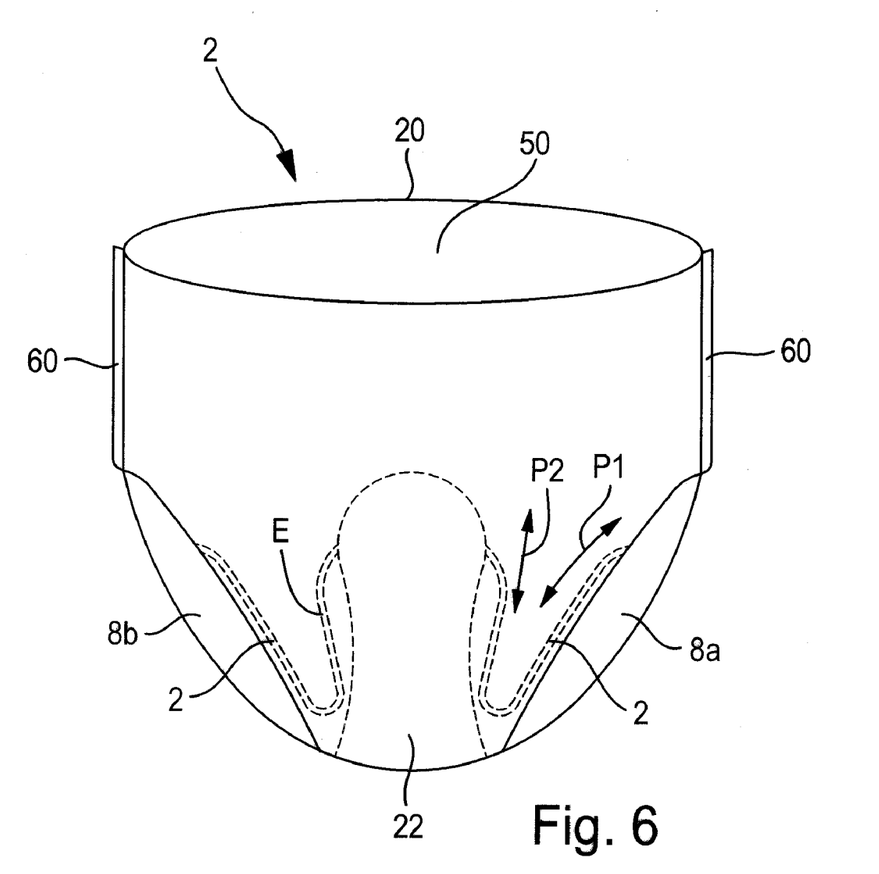
FIG. 6 A perspective view of a sanitary article according to the present disclosure after the longitudinal edge regions have been joined by the manufacturer.

FIG. 5 shows that the respective leg opening 8a, b has different elasticized regions in the front crotch region 10a, namely a region 40 close to the hip opening, a region 42 close to the crotch center, and a central region 41 arranged in between, whereby the region 40 close to the hip opening, the region 42 close to the crotch center, and the central region 41 exhibit strand-shaped elasticizing means 44. The strand size, pretension, direction, and density of the arrangement of the elasticizing means 44 are chosen such that each resulting force of the elasticizing means 44 has one component in the transverse direction 38, and that this component in the transverse direction is larger in the region 40 close to the hip opening than in the central region 41, and that the component in the transverse direction in the central region 41 is larger than in the region 42 close to the crotch center 42. In this way, the fit of the sanitary article around the leg is, in particular, advantageously ensured. In the described case, the elasticizing means 44 in the region 40 of the leg openings 8a, b close to the hip opening are exclusively formed by strand or ribbon-shaped elasticizing means essentially arranged in the transverse direction. The elasticizing means 44 in the central region 41 are formed by a section 1a of the first strand or ribbon-shaped elasticizing means 1 close to the hip opening, as well as by the strand or ribbon-shaped elasticizing means 6 essentially arranged in the transverse direction.

Finally, the elasticizing means 44 in the region 42 close to the crotch center are exclusively formed by a section 1b of the first strand or ribbon-shaped elasticizing means 1 close to the crotch center. A further region 43 joins the region 42 close to the crotch center reaching to the central transverse axis Q, where the leg opening has no elasticizing means at all.

Crotch center is understood to be the section of the crotch region 10 that comprises the central transverse axis Q.

FIGS. 2 and 3 finally show in detail that the absorbent core 22 is underpinned by a liquid impervious backsheet 14 and covered by a liquid pervious topsheet 13. The cuff elements 7 are formed by a hydrophobic nonwoven material and are affixed with their proximal edge 72 to the topsheet 13 on both sides of the absorbent core 22 parallel to the central longitudinal axis. Each distal edge 71 of the cuff elements 7 is provided with an elasticized means, namely a pretensioned elastic strand 73, in a section comprising at least the crotch center, the elastic cuff element 9. By means of the restoring force of the strand, the elastic cuff section 9 may stand upward against the user's skin, as shown in FIG. 3. Each cuff element remains nonelastic in the direction of the front and rear hip edge 20a, 20b and thus forms nonelastic sections there. The distal edge 71 is tilted inward at a rear and front end section 74 of the cuff element 7 and affixed to the topsheet 13 by means of ultrasound welding spots (not shown). Besides, the joint comprises elasticizing means in the form of elastic strands 84 parallel to the central longitudinal axis L which are affixed between the topsheet and backsheet, as shown in FIG. 3. The elasticizing means 84 are preferably arranged outside the proximal edge 72 of the cuff element 7, when viewed in the transverse direction 38, i.e. the elastic strands 84 are arranged closer to the leg openings 8a, b than the proximal edges 72 of the cuff elements 7.

It should be noted that the disclosure is not limited to the embodiments described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:

1. A pants-type disposable absorbent sanitary article comprising:
    an absorption core;
    a chassis-forming outer wrap including
        a continuously closed hip edge forming a hip opening all around the periphery,
        a front region and a back region with longitudinal side edge sections, and
    a crotch region arranged between the front region and the back region and forming leg openings, the leg openings being formed by joining together the longitudinal side edge sections of the front region and the back region of the chassis-forming outer wrap, the crotch region including a front crotch region and a rear crotch region divided by a central transverse axis extending in a transverse direction, the rear crotch region including an outer region and an inner region disposed longitudinally between the outer region and the front crotch region, the leg openings defined by a first section in the front crotch region, a second section in the outer region of the rear crotch region, and a third section in the inner region of the rear crotch region;

first strand or ribbon-shaped elasticizing means which extend exclusively in the front crotch region and which have a part arranged along the first section of the respective leg opening;

second strand or ribbon-shaped elasticizing means which extend exclusively in the outer region of the rear crotch region and which have a first part arranged along the second section of the respective leg opening, and an elastic element which is arranged between the second section of the leg opening and a respective longitudinal edge of the absorbent core, first part and the elastic element forming a u-shaped or v-shaped configuration with an apex disposed adjacent to the inner region, the elastic element extending from the apex with a transverse inward component and with a longitudinal rearward component toward the absorbent core, the second elasticizing means being spaced longitudinally from the first strand or ribbon-shaped elasticizing means.

2. The sanitary article according to claim 1, characterized in that the distance in the transverse direction between the edge of the absorbent core and a respective leg opening is at least about 5 cm in the outer region, in particular at least about 7 cm and furthermore in particular at least about 9 cm.

3. The sanitary article according to claim 1, characterized in that the length of the longitudinal component of the elastic element is about 2.5-21.0 cm, in particular about 4.5-19.0 cm, furthermore in particular about 6.5-17.0 cm, and also in particular about 7.5-15.0 cm.

4. The sanitary article according to claim 3, characterized in that the length of the transverse component of the elastic element is about 2.0-18.0 cm, in particular about 4.0-15.0 cm, furthermore in particular about 5.0-13.0 cm, and also in particular about 6.0-12.0 cm.

5. The sanitary article according to claim 1, characterized in that the inner region of the rear crotch region of a respective leg opening has third strand or ribbon-shaped elasticizing means which have a part arranged along the third section of the respective leg opening.

6. The sanitary article according to claim 5, characterized in that the first and/or second and/or third strand or ribbon-shaped elasticizing means traverse the crotch region underneath the absorbent core from a first leg opening to take a mirror-inverted course relative to the central longitudinal axis along the other second leg opening on the opposite side.

7. The sanitary article according to claim 6, characterized in that the elasticizing effect of the elasticizing means underneath the absorbent core is removed at least in sections by means of heat and/or pressure and/or laser processing and/or ultrasound and/or cutting.

8. The sanitary article according to claim 6, characterized in that the elasticizing means underneath the absorbent core are tension free.

9. The sanitary article according to claim 5, characterized in that in the longitudinal direction the first elasticizing means are at a greater distance from the third elasticizing means than the second elasticizing means from the third elasticizing means.

10. The sanitary article according to claim 5, characterized in that the course of the third elasticizing element is largely mirror-inverted relative to the course of the elastic element, whereby the axis of symmetry is a line running centrally in the transverse direction between the third elasticizing means and the elastic element.

11. The sanitary article according to claim 1, characterized in that the chassis-forming wrap has ribbon or strand-shaped elasticizing means running in the transverse direction in the back region and in the front region, and also in particular in an area of the crotch region adjacent to the back region and/or front region.

12. The sanitary article according to claim 11, characterized in that the elasticizing effect of the ribbon or strand-shaped elasticizing means running in the transverse direction is removed insofar as they run underneath the absorbent core.

13. The sanitary article according to claim 1, characterized in that a respective leg opening in the front crotch region has a region close to the hip opening, a region close to the crotch center, and a region arranged in between, and whereby the region close to the hip opening, the region close to the crotch center and the central region exhibit elasticizing means, and whereby the resultant forces of the elasticizing means respectively have a component in the longitudinal direction, and whereby this component is greater in the longitudinal direction in the region close to the hip opening than in the central region and/or in the region close to the crotch center, and the component in the longitudinal direction is greater in the central region than in the region close to the crotch center.

14. The sanitary article according to claim 13, characterized in that the elasticizing means in the region of the leg openings close to the hip opening are exclusively formed by strand or ribbon-shaped elasticizing means essentially arranged in the transverse direction.

15. The sanitary article according claim 13, characterized in that the elasticizing means are formed in the central region by a section close to the hip opening of the first strand or ribbon-shaped elasticizing means and by strand or ribbon-shaped elasticizing means essentially arranged in the transverse direction.

16. The sanitary article according to claim 13, characterized in that the elasticizing means in the region close to the crotch center are exclusively formed by a section close to the crotch center of the first strand or ribbon-shaped elasticizing means.

17. The sanitary article according to claim 1, characterized in that cuff elements with an elastic cuff section are provided on both sides of the absorbent core and extend in its longitudinal direction.

18. The sanitary article according to claim 1, characterized in that the absorbent core is covered by a topsheet on the body-facing side and underpinned by a backsheet on the garment-facing side.

19. The sanitary article according to claim 1, characterized in that the rear crotch region is longer than the front crotch region.

20. The sanitary article according to claim 5, characterized in that the sum of the lengths of the first to third sections of a respective leg opening is about 20-60 cm, in particular about 25-55 cm, furthermore in particular about 27-50 cm, and also in particular about 29-48 cm.

21. The sanitary article according to claim 5, characterized in that the relationship between the sums of the lengths of the first to third sections of a respective leg opening and the perimeter of a respective leg opening is at most about 0.7, in particular at most about 0.6, furthermore in particular at most about 0.55, and also in particular at most about 0.5.

22. The sanitary article according to claim 1, characterized in that the rear crotch region has a length of about 20-50 cm, in particular of about 22-45 cm, furthermore in particular of about 24-42 cm, and also in particular of about 26-39 cm.

23. The sanitary article according to claim 1, characterized in that the inner region and/or outer region of the rear crotch region have a length of about 8-30 cm, in particular of about 10-25 cm, and furthermore in particular of about 12-22 cm.

24. The sanitary article according to claim 1, characterized in that the relationship between the length of the inner region and the length of the outer region is about 0.4-0.6, in particular about 0.45-0.55 and furthermore in particular about 0.47-0.52.

* * * * *